(12) United States Patent
Wilson

(10) Patent No.: US 6,667,337 B2
(45) Date of Patent: Dec. 23, 2003

(54) COMBINATION THERAPY FOR CANCER

(75) Inventor: William R. Wilson, Auckland (NZ)

(73) Assignee: Cancer Research Technology Limited, London (GB)

( * ) Notice: Subject to any disclaimer, the term of this patent is extended or adjusted under 35 U.S.C. 154(b) by 0 days.

(21) Appl. No.: 09/774,002

(22) Filed: Jan. 31, 2001

(65) Prior Publication Data

US 2001/0027210 A1 Oct. 4, 2001

(30) Foreign Application Priority Data

Mar. 3, 2000 (NZ) ................................................ 503199

(51) Int. Cl.$^7$ ........................ A61K 31/335; A61K 31/35
(52) U.S. Cl. ........................................ 514/449; 514/455
(58) Field of Search ................................ 514/455, 449

(56) References Cited

U.S. PATENT DOCUMENTS

| | | | |
|---|---|---|---|
| 5,281,620 A | | 1/1994 | Denny et al. |
| 5,620,875 A | * | 4/1997 | Hoffman et al. ............ 514/449 |
| 5,817,684 A | | 10/1998 | Fleisch et al. |
| 5,910,505 A | | 6/1999 | Fleisch et al. |
| 2001/0027210 A1 | | 10/2001 | Wilson |

FOREIGN PATENT DOCUMENTS

| | | |
|---|---|---|
| EP | 0 584 001 A1 | 2/1994 |
| EP | 0 743 064 A1 | 11/1996 |
| EP | 0 584 001 B1 | 5/1997 |
| JP | 2001247459 | 11/2001 |
| WO | WO 94/23753 | 10/1994 |
| WO | WO 95/09621 | 4/1995 |
| WO | WO 97/34482 | 9/1997 |
| WO | WO 98/25600 | 6/1998 |
| WO | WO 98/42332 | 10/1998 |
| WO | WO 98/42335 | 10/1998 |
| WO | WO 98/42336 | 10/1998 |
| WO | WO 98/42337 | 10/1998 |
| WO | WO 98/42346 | 10/1998 |
| WO | WO 98/42650 | 10/1998 |
| WO | WO 00/10600 | 3/2000 |
| WO | WO 00/10600 A3 | 3/2000 |
| WO | WO 00/16798 | 3/2000 |
| WO | 00/48591 | 8/2000 |
| WO | WO 00/76497 A1 | 12/2000 |
| WO | WO 01/34135 A2 | 5/2001 |
| WO | WO 01/34137 A2 | 5/2001 |
| WO | WO 01/34197 A2 | 5/2001 |
| WO | WO 01/34198 A2 | 5/2001 |
| WO | WO 02/09700 | 2/2002 |

OTHER PUBLICATIONS

Hill, Sally A. et al, Int. J. Cancer, vol. 63, No. 1, pp. 119–123 (1995).
Chaplin, D.J. et al, Proc. Annu. Am. Assoc. Cancer Res, vol. 37–A3009 (1996).
Pruijin, Frederik B. et al, Cancer Chemother Pharmacol, vol. 39, pp. 541–546 (1997).
Vincent, Patrick W. et al, Oncol. Rep., vol. 4, No. 1, pp. 143–147 (1997).
Combretastatin Updated: Preliminary Results from Ohio Phase 1 Trial Show Tumors Respond, Patients Experience Vascular Stress, PSA Rising: Medical Pike Briefs: Headline Index: Clinical Trial Phase 1 Results, Nov. 8, 1999, available at psa–rising.com/medical/combretastatinupdate.htm.
Kanwar, et al; "Taking lessons from dendritic cells: multiple . . . anti–tumor immunity"; Gene Therapy, 1999; 6: 1835–1844.
Kanwar, et al; "Vascular Attack by 5,6–Dimethylxanthenone–4–acetic Acid . . . Tumors and Multiple Tumor Foci$^{1}$", Cancer Resh., 2001; 61: 1948–1956.
Hornung, et al; "Augmentation of Natural Killer Activity, Induction . . . Using Flavone Acetic Acid and IL–2$^{1,2}$", The Journal of Immunology (1988); vol. 141(10), pp. 3671–3679.
Thomsen, et al; "Nitric Oxide Production in Endotoxin–Resistant . . . Acid Analogues"; Biochem. Pharmacol, 43: 11; 1992; pp. 2401–2406.

(List continued on next page.)

Primary Examiner—Jerome D. Goldberg
(74) Attorney, Agent, or Firm—Nixon & Vanderhye

(57) ABSTRACT

This invention relates to a method of treating cancer, and particularly a method including the steps of administering to a mammal in need of such treatment, either simultaneously or sequentially, (i) a compound selected from a paclitaxel and docetaxel, and (ii) a compound of the formula (I)

or a pharmaceutically acceptable salt or ester thereof;
wherein $R_1$, $R_2$ and $R_3$ are each independently selected from the group consisting of H, $C_1$–$C_6$ alkyl, halogen, $CF_3$, CN, $NO_2$, $NH_2$, OH, OR, NHCOR, $NHSO_2R$, SR, $SO_2R$ or NHR, wherein each R is independently $C_1$–$C_6$ alkyl optionally substituted with one or more substituents selected from hydroxy, amino and methoxy, and wherein each of $R_1$, $R_2$ and $R_3$ may be present at any of the available positions 1 to 8;
and wherein in each of the carbocyclic aromatic rings in formula (I), up to two of the methine (—CH=) groups may be replaced by an aza (—N=) group;
and wherein any two of $R_1$, $R_2$ and $R_3$ may additionally together represent the group —CH=CH—CH=CH—, such that this group, together with the carbon or nitrogen atoms to which it is attached, forms a fused 6 membered aromatic ring.

5 Claims, 1 Drawing Sheet

OTHER PUBLICATIONS

Lash, et al; "Enhancement of the anti–tumour effects . . . and ioreductive drugs"; Br. J. Cancer, 78: pp. 439–445, 1998.

Pedley, et al; "Enhancement of Antibody–directed Enzyme . . . by an Antivascular Agent[1]", Cancer Res., 59: pp. 3998–4003; 1999.

Pruijn, et al; "Mechanisms of enhancement of the antitumour . . . 5,6–dimethylxanthenone–4–acetic acid"; Cancer Chemother Pharmacol, (1997) 39: pp. 541–546.

Cliffe, et al; "Combining Bioreductive Drugs . . . or 5,6–Dimethylxanthenone Acetic Acid"; Int. J. Rdiation Oncology Biol. Phys., 29: pp. 373–377, 1994.

Phillips; "Inhibition of DT–diaphorase (NAD(P)H:Quinone Oxidoreductase . . . for Bioreductive Drug Development"; Biochem. Pharmacol., 58: pp. 303–310, 1999.

Ching, et al; "Effect of thalidomide on tumour necrosis . . . induced by 5,6–dimethylxanthenone–4–acetic acid"; Br. J. Cancer, 72: pp. 339–343, 1995.

Browne, et al; "Suppression of Serum Tumour Necrosis Factor0α . . . Activity of 5,6–Dimethylxanthenone–4–Acetic Acid"; Anticancer Res., 18: pp. 4409–4414, 1998.

Ching, et al; "Interaction of thalidomide, phthalimide analogues . . . and enhancement of anti–tumour activity"; Br. J. Cancer, 78: pp. 336–343, 1998.

Kestell, et al; "Modulation of the pharmacokinetics of . . . acid (DMXAA) in mice by thalidomide"; Cancer Chemother. Pharmacol., 45: 135–141, 2000.

Cao, et al; "Thalidomide increases both intr–tumoural tumour necrosis . . . in response to 5,6–dimethylxanthenone–4–acetic acid"; Br. J. Cancer, 80: pp. 716–723, 1999.

Baguley, et al; "Serotonin involvement in the antitumour . . . and 5,6–dimethylxanthenone–4–acetic acid"; Br. J. Cancer, 80: pp. 716–723, 1999.

Zwi, et al; "Correlation Between Immune and Vascular Activityes of Xanthenone Acetic Acid Antitumor Agents"; Oncol. Res., 6: pp. 79–85, 1994.

Zhao, et al; Effects of the serotonin receptor antagonist . . . of 5,6–dimethylxanthenone–4–acetic acid (DMXAA); Cancer Chemother. Pharmacol., 47: pp. 491–497, 2001.

Futami, et al; "Cytokine Induction and Therapeutic . . . by Xanthenone–4–Acetic Acid Derivatives"; J. Immunother., 12: pp. 247–255, 1992.

Ching, et al; "Interaction between endotoxin and the anti–tumour agent . . . necrosis of colon 38 tumours"; Cancer Chemother. Pharmacol., 35: pp. 153–160, 1994.

Ching, et al; Induction of Intratumoral Tumor Necrosis Factor (TNF) . . . Acid (DMXAA) in TNF Knockout Mice[1]; Cancer Res., 59: pp. 3304–3307, 1999.

Thomsen; et al; Tumor–dependent Increased Plasma Nitrate Concentrations . . . and analogues in Mice[1]; Cancer Res., 51: pp. 77–81, 1991.

Baguley, et al; "Evidence that the 5–hydroxytryptamine antagonist, cyproheptadine . . . vinblastine and other agents"; In: S., Moncada, M.A., Marletta, J.B., Hibbs, Jr., and E.A. Higgs (eds) Biology of Nitric Oxide Part 2. Enzymology, Biochemistry and Immunology pp. 222–224, London: Portland Press, 1992.

Fujii H., et al; "Vaccination with B7–18 tumor and anti–adhesion therapy with RGD pseudo–peptide (FC–336) efficiently induce anti–metastatic effect"; Clinical & Experimental Metastasis, (1998), vol. 16, pp. 141–148.

Zitvogel, L.; "Interleukin–12 and b7.1 co–stimulation cooperate in the induction of effective antitumor immunity and therapy of established tumor"; Journal of Immunology, (1996), vol. 26, pp. 1335–1341.

Lissoni, P., et al; "Neuroimmunotherapy of advanced solid neoplasms with single evening subcutaneous injection of low–dose interleukin–2 and melatonin preliminary results"; European Journal of Cancer, (1993), vol. 29A(2), pp. 185–189.

Nawrocki, S., and Mackiewicz A., "Genetically modified tumour vaccines—where we are today," Cancer Treatment Reviews, (1999), vol. 25, pp. 29–46.

Thrash–Bingham, C.A. and Tartof, K.D., "aHIF: A natural antisense transcript overexpressed in human renal cancer during hypoxia"; The Journal of the National Cancer Institute, (1999), vol. 91(2), pp. 143–151.

Chaplin, D.J., et al; Proc. Annu. Meet. Am. Assoc. Cancer Res., Mar. 1996, vol. 37, #3009, "Antivascular approaches to solid tumour therapy; evaluation of tubulin binding agents".

Rustin, G.; "Vascular Targeting in the Clinic"; Abstract; ICTR 2000; 1$^{st}$ Int'l Conference on Translational Research A.

Baguley, B.C., et al; "291 Mechanisms of tumour blood flow inhibition by the antitumour drug DMXAA (5,6–dimethylxanthenone–4–acetic acid"; Preceedings of the 11$^{th}$ NCI EORTC AACR Symposium; Copyright ®2000 Stichting NCI–EORTC Symposium on New Drugs in Cancer Therapy; Publ. by the AACR; Published as a Supplement to Clinical Cancer Research, vol. 6, Nov. 2000.

Zhou, et al; Answer 1 of 81; Caplus 2001: 422777; "A difference between the rat and mouse in the pharmacokinetic interaction of 5,6–*dimethylxanthenone*–4–acetic acid with thalidomide"; Cancer Chemother. Pharmacol. (2001), 47(6), 541–544; abstract.

Zhao, et al; Answer 2 of 81; Caplus 2001:422769; Effects of the serotonin . . . *dimethylxanthenone*–4–acetic acid (*DMXAA*); Cancer Chemother. Pharmacol. (2001), 47(6), 491–497; abstract.

Zhou, et al; Answer 3 of 81; Caplus; 2001:352622; Determination of unbound concentration of the novel . . . liquid chromatography with fluorimetric detection; J. Chromatogr., B: Biomed. Sci. Appl. (2001), 757(2), 359–363; abstract.

Zhou, et al; Answer 4 of 81; Caplus 2001:352620; Determination of the covalent adducts . . . samples by high–performance liquid chromatography; J. Chromatogr., B: Biomed. Sci. Appl. (2001), 757(2), 343–348; abstract.

Zhou, et al; Answer 5 of 81; Caplus 2001:348171; "Reversible binding of the novel anti–tumour agent . . . and its distribution into blood cells in various species"; J. Pharm. Pharmacol. (2001), 53(4), 463–471; abstract.

Zhou, et al; Answer 6 of 81; Caplus 2001:324235; "In vitro and in vivo kinetic interactions . . . –4–acetic acid with thalidomide and diclofenac"; Cancer Chemother. Pharmacol. (2001), 47(4), 319–326; abstract.

Kanwar, et al; Answer 7 of 81; Caplus 2001:227306; "Vascular attack by 5,6–*dimethylxanthenone* . . . leads to the eradication of large tumors and multiple tumore foci"; Cancer Res. (2001), 61(5), 1948–1956; abstract.

Cao, et al; Answer 8 of 81; Caplus 2001:183669; "Interferon–inducible protein 10 induction . . . –4–acetic acid (*DMXA*)"; Cancer Res. (2001), 61(4), 1517–1521; abstract.

Murata, et al; Answer 9 of 81; Caplus 2001:175425; "Comparative effects of combretastatin A-4 disodium phosophate . . . -4-acetic acid on blood perfusion in a murine tumour and normal tissues"; Int. J. Radiat. Biol. (2001), 77(2), 195-204; abstract.

Zhou, et al; Answer 10 of 81; Caplus 2000:860808; "Identification of the human liver cytochrome P450 . . . -4-acetic acid"; Drug Metab. Dispos. (2000), 28(12), 1449-1456; abstract.

Slim, et al; Answer 11 of 81; Caplus 2000-642218; "Scintigraphic imaging of the hypoxia marker 99mtechnetium-labeled antivascular agent 5,6-*dimethylxanthenone*-4-acetic acid"; Cancer Res. (2000), 60(16), 4582-4588; abstract.

Kestell, et al; Answer 12 of 81; Caplus 2000:516217; "Modulation of the pharmacokinetics of the antitumor agent . . . in mice by thalidomide"; Cancer Chemother. Pharmacol. (2000), 46(2), 135-141; abstract.

Aitken, et al; Answer 13 of 81; Caplus 2000:459208; "Synthesis and antitumor activity of new derivatives of flavone-8-acetic acid (FAA), Part 4: variation of the basic structure"; Arch. Pharm. (Weinheim, Ger.) (2000), 333(6), 181-188; abstract.

Zhou, et al; Answer 14 of 81; Caplus 1999:765284; "Determination of two major metabolites of the novel . . . acid in hepatic microsomal incubations by high-performance liquid chromatogrpaty with fluorescence detection"; J. Chromatogr., B: Biomed. Sci. Appl. (1999), 734(1), 129-136; abstract.

Ching, et al; Answer 16 of 81; Caplus 1999:538562; "Induction of STAT and NF-kappa.B activation by the antitumor agents . . . -4-acetic acid and flavone acetic acid in a murine marophage cell line"; Biochem. Pharmacol. (1999), 58(7), 1173-1181; abstract.

Ching, et al; Answer 17 of 81: Caplus 1999:467500; "Induction of intratumoral tumor necrosis factor (TNF) synethesis and . . . -4-acetic acid (*DMXAA*) in TNF knockout mice"; Cancer Res. (1999), 59(14), 3304-3307; abstract.

Phillips, Roger M.; Answer 18 of 81; Caplus 1999:400010; "Inhibition of DT-diaphorase (NAD (P) H:quinone oxidoreductase, EC 1.6.99.2) by 5,6-*dimethylxanthenone*-4-acetic acid (*DMXAA*) and . . . bioreductive drug development"; Biochem. Pharmacol. (1999), 58(2), 303-310; abstract.

Cao, et al; Answer 19 of 81; Caplus 1999:349887; "Thalidomide increases both intra-tumoral tumor necrosis factor-.alpha.production and antitumor activity in response to 5,6-*dimethylxanthenone*-4-acetic acid"; Br. J. Cancer (1999), 80(5/6), 716-723; abstract.

Kestell, et al; Answer 20 of 81; Caplus 1999:191815; "Plasma disposition, metabolism, and excretion of the . . . -4-acetic acid in the mouse, rat, and rabbit"; Cancer Chemother. Pharmacol. (1999), 43(4), 323-330; abstract.

Joseph, et al; Answer 21 of 81; Caplus 1999:109860; "Stimulation of tumors to synthesize tumor . . . -4-acetic acid; a novel approach to cancer therapy"; Cancer Res. (1999), 59(3), 633-638; abstract.

Browne, et al; Answer 22 of 81; Caplus 1999:68223; "Suppression of serum tumor necrosis factor-. alpha. by thalidomide does not lead to reversal of tumor vascular collapse and anti-tumor activity of 5,6-*dimethylxanthenone*-4-acetic acid"; Anticancer Res. (1998), 18(6A), 4409-4413; abstract.

Wilson, et al; Answer 23 of 81; Caplus 1999:5894; "Enhancement of tumor radiation response by the antivascular agent 5,6-*dimethylxanthenone*-4-acetic acid"; Int. J. Radiat. Oncol., Biol., Phys. (1998), 42(4), 905-908; abstract.

Zaks-Zilberman, et al; Answer 24 of 81; Caplus, 1998:649593; "Induction of adrenomedullin mRNA and protein by lipopolysaccharide and paclitaxel (taxol) in murine macrophages"; Infect. Immun. (1998), 66(10), 4669-4675; abstract.

Lash., et al; Answer 25 of 81; Caplus 1998:571075; "Enhancement of the anti-tumor effects of the antivascular agent . . . by combination with 5-hydroxytryptamine and bioreductive drugs"; Br. J. Cancer (1998), 78(4), 439-445; abstract.

Pang, et al; Answer 26 of 81; Caplus 1998:534308; "Antitumor activity of the novel immune modulator 5,6-*dimethylxanthenone*-4-acetic acid (*DMXAA*) in mice lacking the interferon-gamma receptor"; Eur. J. Cancer (1998), 34(8), 1282-1289; abstract.

Ching, et al; Answer 27 of 81; Caplus 1998:533041; "Interaction of thalidomide, phthalimide analogs of thalidomide and pentoxifylline with the anti-tumor agent 5,6-*dimethylxanthenone* . . . necrosis factor-alpha and enhancement of anti-tumor activity"; Br. J. Cancer (1998), 78(3), 336-343; abstract.

Baguley, et al; Answer 28 of 81; Caplus 1998:426219; "Immunomodulatory actions of xanthenone anticancer agents"; BioDrugs (1997), 8(2), 119-127; abstract.

Slim, et al; Answer 29 of 81; Caplus 1998:145311; "Nitro reduction as an electronic switch for bioreductive drug activation"; Oncol. Res. (1997), 9(6/7), 357-369; abstract.

Baguley, et al; Answer 30 of 81; Caplus 1998:145286; "Increased plasma serotonin following treatment with flavone-8-acetic acid, 5,6-. . . colchicine; relation to vascular effects"; Oncol. Res. (1997), 9(2), 55-60; abstract.

Moilanen, et al; Answer 31 of 81; Caplus 1998:109247; "Persistent induction of nitric oxide synthase in tumors from mice treated with the anti-tumor agent 5,6-*dimethylxanthenone*-4-acetic acid"; Br. J. Cancer (1998), 77(3), 426-433; abstract.

Philpott, et al; Answer 32 of 81; Caplus 1998:43376; "Production of tumor necrosis factor-.alpha. by cultured human peripheral blood leukocytes in response to the anti-tumor agent 5,6-*dimethylxanthenone*-4-acetic acid (NSC 640488)"; Br. J. Cancer (1997), 76(12), 1586-1591; abstract.

Everett, et al; Answer 33 of 81; Caplus 1997:419257; "High-performance ion chromatography applied to free-radical mechanisms in drug design. The problem of ion analysis at high ionic strengths"; J. Chromatogr., A (1997), 770(1+2), 273-279; abstract.

Pruijn, et al; Answer 34 of 81; Caplus 1997:262052; "Mechanisms of enhancement of the antitumor activity of melphalan by the tumor-blood-flow inhibitor 5,6-*dimethylxanthenone*-4-acetic acid"; Cancer Chemother. Pharmacol. (1997), 39(6); 541-546; abstract.

Patel, et al; Answer 35 of 81; Caplus 1997:198501; "The effect of 5,6-*dimethylxanthenone*-4-acetic acid on tumor necrosis factor production by human immune cells"; Anticancer Res. (1997), 17 (1A), 141-150; abstract.

Vincent, et al; Answer 36 of 81; Caplus 1997:83756; "Chemotherapy with *DMXAA* (5,6-*dimethylxanthenone*-4-acetic acid) in combination with CI-1010 . . . against advanced stage murine colon carcinoma 26", Oncol. Rep. (1997), 4(1),143–147; abstract.

Miners, et al; Answer 37 of 81; Caplus 1997:71622; "Preclinical prediction of factors influencing the elimination of 5,6-*dimethylxanthenone*-4-acetic acid, a new anticancer drug"; Cancer Res. (1997), 57(2), 284–289; abstract.

Watts, et al; Answer 38 of 81; Caplus 1996:492701; "Changes in coagulation and permeability properties of human endothelial cells in vitro induced by TNF-.alpha, or 5,6 *MeXAA*", Br. J. Cancer, Suppl. (1996), 74(27), S164–S167; abstract.

Wilson, et al; Answer 39 of 81; Caplus 1996:492687; "Tertiary amine N-oxides as bioreductive drugs; DACA N-oxide, nitracrine N-oxide and AQ4N"; Br. J. Cancer, Suppl. (1996), 74(27), S43–S47; abstract.

Pedley, et al; Answer 40 of 81; Caplus 1996:432950; "Ablation of colorectal xenografts with combined radioimmunotherapy and tumor blood flow–modifying agents"; Cancer Res. (1996), 56(14), 3293–3300; abstract.

Wilson, et al; Answer 41 of 81; Caplus 1995:953723; "Hypoxia–activated prodrugs as antitumor agents: strategies for maximizing tumor cell killing"; Clin. Exp. Pharmacol. Physiol. (1995), 22(11), 881–5; abstract.

Hill, et al; Answer 42 of 81; Caplus 1995:938958; "Anti–vascular approaches to solid tumor therapy: Evaluation of vinblastine and flavone acetic acid"; Int. J. Cancer (1995), 63(1), 119–23; abstract.

Ching, et al; Answer 43 of 81; Caplus 1995:750173; "Effect of thalidomide on tumor necrosis factor production and antitumor activity induced by 5,6-*dimethylxanthenone*-4-acetic acid"; Br. J. Cancer (1995), 72(2), 339–43; abstract.

Philpott, et al; Answer 44 of 81; Caplus 1995:724307; "Induction of tumor nerosis factor–alpha. by single and repeated doses of the antitumor agent 5,6-*dimethylxanthenone*-4-acetic acid"; Cancer Chemother. Pharmacol. (1995), 36(2), 143–8; abstract.

Laws, et al; Answer 45 of 81; Caplus 1995:674435; "Preclinical in vitro and in vivo activity of 5,6-*dimethylxanthenone*-4-acetic acid"; Br. J. Cancer (1995), 71(6), 1204–9; abstract.

Thomsen, et al; Answer 58 of 81; Caplus 1994:124393; "Nitric oxide: its production in host–cell–infiltrated EMT6 spheroids and its role in tumor cell killing by flavone-8-acetic acid and 5,6-*dimethylxanthenone *-4-acetic acid"; Cancer Chemother. Pharmacol. (1992), 31(2), 151–5; abstract.

Baguley, et al; Answer 59 of 81; Caplus 1993:440398; "Evidence that the 5-hydroxytryptamine antagonist, cyproheptadine, modulates nitric oxide production in mice in response to flavone acetic acid, vinblastine and other agents"; Biol. Nitric Oxide, Proc. Int. Meet., 2$^{nd}$ (1992), Meeting Date 1991, vol. 2, 222–4. Eds.: Moncada, Salvador. Publisher: Portland Press, London, UK.; abstract.

Veszelovszky, et al; Answer 60 of 81; Caplus 1993:204708; "Flavone acetic acid and 5,6-*dimethylxanthenone*-4-acetic acid; relationship between plasma nitrate elevation and the induction of tumor necrosis"; Eur. J. Cancer, Part A (1993), 29A(3), 404–8; abstract.

Futami, et al; Answer 61 of 81; Caplus 1993:139339; "Cytokine induction and therapeutic synergy with interleukin-2 against murine renal and colon cancers by *xanthenone*-*4*-*acetic* acid derivatives"; J. Immunother. (1992), 12(4), 247–5; abstract.

Gamage, et al; Answer 62 of 81; Caplus 1993:80787; "Structure–activity relationship for substituted 9-oxo-9, 10–dihydroacridine-4-acetic acids: analogs of the colon tumore active agent *xanthenone*-*4*-*acetic* acid"; Anti-Cancer Drug Des. (1992), 7(5), 403–14; abstract.

Ching, et al; Answer 63 of 81; Caplus 1992:604666; "Antitumor responses to flavone-8-acetic acid . . . in immune–deficient mice"; Br. J. Cancer (1992), 66(1), 128–30; abstract.

Ching, et al; Answer 64 of 81; Caplus 1992:503777; "Stimulation of macrophage tumoricidal activity by 5,6-*dimethylxanthenone*-4-acetic acid, a potent analog of the antitumor agent flavone-8-acetic acid"; Biochem. Pharmacol. (1992), 44(1), 192–5; abstract.

Thomsen, et al; Answer 65 of 81; Caplus 1992:503711; "Nitric oxide production in endotoxin–resistant C3H/HeJ mice stimulated with flavone-8-acetic acid and *xanthenone*-*4*-*acetic* acid analogs"; Biochem. Pharmacol. (1992), 43(11), 2401–06; abstract.

Thomsen, et al; Answer 66 of 81; Caplus 1992:165869; "Modulation of superoxide production from murine macrophages by the antitumor agent flavone acetic acid and *xanthenone* *acetic* acid analogs"; Biochem. Pharmacol. (1992), 43(2), 386–9; abstract.

Ching, et al; Answer 67 of 81; Caplus 1992:243202; "In vitro methods for screening agents with an indirect mechanism of antitumor activity: xanthenone analogs of flavone acetic acid"; Eur. J. Cancer (1991), 27(12), 1684–9; abstract.

Ching, et al; Answer 68 of 81; Caplus 1992:51034; "Hemotological effects in mice of the antitumor agents *xanthenone*-*4*-*acetic*acid, 5,6-*dimethylxanthenone*-4-acetic acid and flavoneacetic acid"; Cancer Chemother. Pharmacol. (1991), 28(6), 414–19; abstract.

Ching, et al; Answer 46 of 81; Caplus 1995:535833; "Interaction between endotoxin and the antitumor agent 5,6-*dimethylxanthenone*-4-acetic acid in the induction of tumor"; Cancer Chemother. Pharmacol. (1994), 35(2), 153–60; abstract.

Webster, et al; Answer 47 of 81; Caplus 1995:443204; "Metabolism and elimination of 5,6-*dimethylxanthenone*-4-acetic acid in the isolated perfused rat liver"; Drug Metab. Dispos. (1995), 23(3), 363–8; abstract.

Perera, et al; Answer 48 of 81; Caplus 1995:223939; "Activation of LPS–inducible genes by the antitumor agent 5,6-*dimethylxanthenone*-4-acetic acid in primary murine macrophages. Dissection of signaling pathways leading to gene induction and tyrosine phosphorylation"; J. Immunol. (1994), 153(10), 4684–93; abstract.

Zwi, et al; Answer 49 of 81; Caplus 1995:197516; The morphological effects of the antitumor agents flavone acetic acid and 5,6-*dimethyl* *xanthenone* *acetic* acid on the colon 38 mouse tumor; Pathology (1994), 26(2), 161–9, abstract.

Zwi, et al; Answer 50 of 81; Caplus 1994:645372; "Correlation between immune and vascular activities of xanthenoneacetic acid antitumor agents"; Oncol. Res. (1994), 6(2), 79–85; abstract.

Kestell, et al; Answer 51 of 81; Caplus 1994:644972; "Disposition of the novel antitumor agent *xanthenone*–*4*–*acetic* acid in the mouse: identification of metabolites and routes of elimination"; Xenobiotica (1994), 24(7), 635–647; abstract.

Pedley, et al; Answer 52 of 81; Caplus 1994:599737; "Enhancement of radioimmunotherapy by drugs modifying tumor blood flow in a colonic xenograft model"; Int. J. Cancer (1994), 57(6), 830–5; abstract.

Cliffe, et al; Answer 53 of 81; Caplus 1994:595143; "Combining bioreductive drugs (SR 4233 or SN 23862) with the vasoactive agents flavone acetic acid or 5,6–*dimethylxanthenone* acetic acid"; Int. J. Radiat. Oncol., Biol., Phys. (1994), 29(2), 373–7; abstract.

Baguley, et al; Answer 54 of 81; Caplus 1994:595115; "Serotonin involvement in the antitumor and host effects of flavone–8–acetic acid and 5,6–*dimethylxanthenone*–4–acetic acid"; Cancer Chemother. Pharmacol. (1993), 33(1), 77–81; abstract.

Everett, et al; Answer 55 of 81; Caplus 1994:499154; "Decarboxylation of the antitumor drugs flavone–8–acetic acid and *xanthenone*–4*–*acetic*** acid by nitrogen dioxide"; Anti–Cancer Drug Des. (1994), 91(1), 68–72; abstract.

Ching, et al; Answer 56 of 81; Caplus 1994:315345; "Effect of tumor growth on the macrophage response to the antitumor agent 5,6–*dimethylxanthenone*–4–acetic acid"; Anticancer Res. (1993), 13(6A), 2069–75; abstract.

Ching, et al; Answer 57 of 81; Caplus 1994:208087; "Induction of tumor necrosis factor–.alpha.messenger RNA in human and murine cells by the flavone acetic acid analog 5,6–*dimethylxanthenone*–4–acetic acid (NSC 640488)"; Cancer Res. (1994), 54(4), 870–2, abstract.

McKeage, et al; Answer 69 of 81; Caplus 1992:15300; "Plasma pharmacokinetics of the antitumor agents 5,6–*dimethylxanthenone*–4–acetic acid, *xanthenone–*4*–*acetic* acid and flavone–8–acetic acid in mice"; Cancer Chemother. Pharmacol. (1991), 28(6), 409–13; abstract.

Rewcastle, et al; Answer 70 of 81; Caplus 1991:535875; "Potential antitumor agents. 63. Structure–activity relationships for side–chain analogs of the colon 38 active agent 9–oxo–9H–xanthene–4–acetic acid"; J. Med. Chem. (1991), 34(9), 2864–70; abstract.

Zwi, et al; Answer 71 of 81; Caplus 1991:526486; "Necrosis in nontumor tissues caused by flavone acetic acid and 5,6–*dimethylxanthenone* acetic acid"; Br. J. Cancer (1990), 62(6), 932–4; abstract.

Ching, et al; Answer 72 of 81; Caplus 1991:441427; "Induction of natural killer activity by xanthenone analogs of flavone acetic acid: relation with antitumor activity"; Eur. J. Cancer (1991), 27(1), 79–83; abstract.

Kestell, et al; Answer 73 of 81; Caplus 1991:177788; "Determination of *xanthenone*–*4*–*acetic* acid in mouse plasma by high–performance liquid chromatography"; J. Chromatogr. (1991), 564(1), 315–21; abstract.

Thomsen, et al; Answer 74 of 81; Caplus 1991:156718; "Tumor–dependent increased plasma nitrate concentrations as an indication of the antitumor effect of flavone–8–acetic acid and analogs in mice"; Cancer Res. (1991), 51(1), 77–81; abstract.

Thomsen, et al; Answer 75 of 81; Caplus 1991:74808; "Evidence for the production of nitric oxide by activated macrophages treated with the antitumor agents flavone–8–acetic acid and *xanthenone*–*4*–*acetic* acid"; Cancer Res. (1990), 50(21), 6966–70; abstract.

Rewcastle, et al; Answer 76 of 81; Caplus 1991:35415; "Potential antitumor agents. 61. Structure–activity relationships for in vivo colon 38 activity among distributed 9–oxo–9H–xanthene–4–acetic acids"; J. Med. Chem. (1991), 34(1), 217–22; abstract.

Rewcastle, Gordon W.; Answer 77 of 81; Caplus 1990:631318; "Synthesis and development of two new classes of anticancer drugs: the tricyclic carboxamides and the xanthenoneacetic acids"; Chem. N.Z. (1989), 53(6), 145–50; abstract.

Rewcastle, et al; Answer 78 of 81; Caplus 1990:503264; "Light–induced breakdown of flavoneacetic acid and xanthenone analogs in solution"; J. Natl. Cancer Inst. (1990), 82(6), 528–9; abstract.

Atwell, et al; Answer 79 of 81; Caplus 1990:91211; "Synthesis and antitumor activity of topologically–related analogs of flavvoneacetic acid"; Anti–Cancer Drug Des. (1989), 4(2), 161–9; abstract.

Van der Auwera, et al; Answer 80 of 81; Caplus 1989:554340; "Conformational features of four model tripeptides having Piv–Pro–*MeXaa* –NMe2 sequences"; Bull. Soc. Chim.Belg.; (1988), 97(3), 199–207; abstract.

Rewcastle, et al; Answer 81 of 81; Caplus 1989:173045; "Potential antitumor agents. 58. Synthesis and structure–activity relationships of substituted *xanthenone*–*4*–*acetic* acids active against the colon 38 tumor in vivo"; J. Med. Chem. (1989), 32(4), 793–9; abstract.

Wilson, "Combination of the Antivascular Agent DMXAA with Radiation and Chemotherapy", *International Journal of Radiation Oncology, Biology and Physics*, vol. 46, No. 3, Feb. 1, 2000, abstract 46, p. 706.

* cited by examiner

COMBINATION THERAPY FOR CANCER

FIELD OF HE INVENTION

This invention relates to a method of treating cancer.

BACKGROUND OF THE INVENTION

The compound 5,6-dimethylanthenone-4-acetic acid PMAA) is known to have significant antitumour activity against murine turmous and human turmours xenografted in immunodeficient mice. Studies have shown that this activity is largely, if not entirely, a consequence of inhibition of blood flow selectively within tumours. However, to date, DMXAA has shown little evidence of clinically viable anti-cancer activity in humans.

The applicants have now surprisingly found that simultaneous or sequential administration of both a compound of the xanthenone acetic acid class (of which DMXAA is one) and either paclitaxel or docetaxel (both compounds of the taxane class of anticancer agents) results in an increase in antitumour activity such that the anticancer effect of the combination is much larger than for either agent alone, and greatly exceeds the sum of effects of the individual agents.

With this background in mind, it was an object of the present invention to provide a method of treatment of cancer which will at least provide the public with a useful choice.

SUMMARY OF THE INVENTION

Accordingly, in a first aspect, the present invention provides a method of treating cancer, the method comprising the step of administering to a mammal in need of such treatment, either simultaneously or sequentially, (i) a compound selected from paclitaxel and docetaxel, and (ii) a compound of the formula

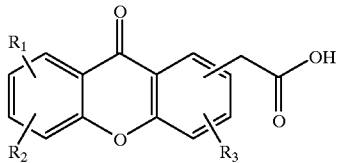

(I)

or a pharmaceutically acceptable salt or ester thereof,
  wherein $R_1$, $R_2$ and R3 are each independently selected from the group consisting of H. $C_1$—$C_6$ alkyl, halogen, CF3, CN, NO2, NH2, OH, OR, NHCOR, $NHSO_2R$, SR, SO2R or NHR, wherein each R is independently C1—C6 alkyl optionally substituted with one or more substituents selected from hydroxy, amino and methoxy, and wherein each of R1, R2 and R3 may be present at any of the available positions 1 to 8;
  and wherein in each of the carbocyclic aromatic rings in formula (I), up to two of the methine (-CH=) groups may be replaced by an aza (-N=) group;
  and wherein any two of $R_1$, $R_2$ and $R_3$ may additionally together represent the group —CH=CH—CH=CH—, such that this group, together with the carbon or nitrogen atoms to which it is attached, forms a fused 6 membered aromatic ring.

Preferably, the mammal is a human.
Preferably, the compound of formula (I) is of the formula:

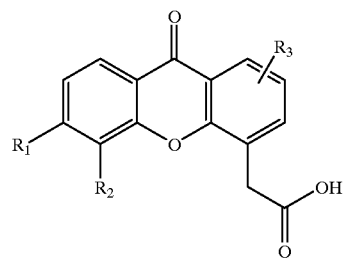

(Ia)

Most preferably, the compound of formula (I) is 5,6-dimethylxanthenone-4-acetic acid, having the formula

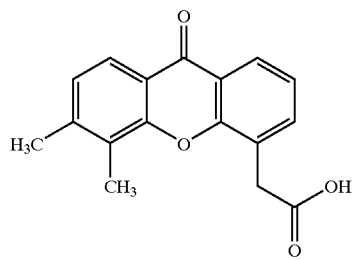

DMXAA

In a further aspect, the present invention provides the use of a compound of the formula (I) as defined above, or a pharmaceutically acceptable salt or ester thereof, in the manufacture of a medicament for treating cancer in a mammal by sequential or simultaneous co-administration of the medicament and a compound selected from paclitaxel and docetaxel.

In still a further aspect, the present invention provides the use of a compound selected from docetaxel and paclitaxel in the manufacture of a medicament for treating cancer in a mammal by sequential or simultaneous co-administration of the medicament and a compound of the formula (I) as defined above or a pharmaceutically acceptable salt or ester thereof.

In yet a further aspect, the present invention provides a pharmaceutical composition suitable for treating cancer, comprising a compound of the formula (I) as defined above or a pharmaceutically acceptable salt or ester thereof, and a compound selected from paclitaxel and docetaxel, in combination with one or more pharmaceutically acceptable carriers or vehicles.

DESCRIPTION OF THE DRAWINGS

While the invention is broadly as defined above, it also includes embodiments of which the following description provides examples. These specific embodiments are described in conjunction with the accompanying drawings in which.

DESCRIPTION OF THE INVENTION

Figure 1:
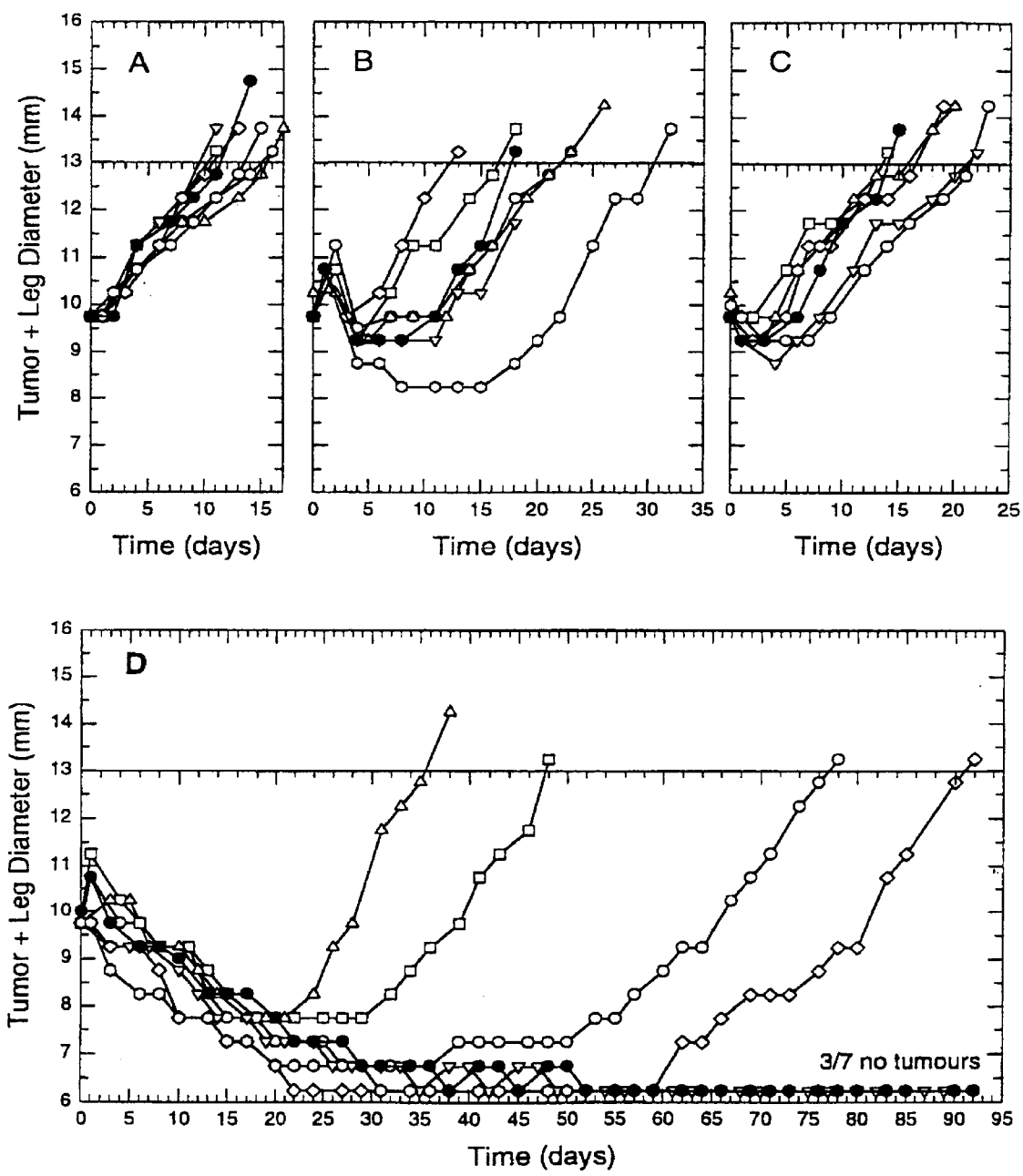
FIG. 1 shows representative individual tumour growth curves for female $C_3H$/HeN mice to which DMXAA, paclitaxel and DMXAA, and paclitaxel were administered as described in Example 1 herein, as follows: A: controls, B: DMXAA (80 μmol/lcg, C: pachitaxel (42.1 μmol/kg), D: DMXAA (80 μmol/kg)+paclitaxel (31.6 μmol/kg).

As defined above, the present invention relates to a method of treating cancer.

The invention resides in the applicant's unexpected finding of a very large synergistic interaction between compounds of the xanthenone acetic acid class having the formula (I) as defined above and two compounds (paclitaxel and docetaxel) of the taxane class of anticancer agents. In particular, the simultaneous administration of both the compound of formula (I) 5,6-dimethylxanthenone-4-acetic acid (DMXAA), and either paclitaxel or docetaxel shows greater toxicity to the host animal than either agent alone (as determined by body weight loss and proportion of deaths) and requires modest reduction in the dose of one or other agent in the combination. However, this host toxicity interaction is much less pronounced than the increase in antitumour activity. As a result, the anticancer effect achieved is dramatically larger than for either agent alone, and greatly exceeds the sum of effects of the individual agents. The combination of 5,6-dimethylxanthenone-4-acetic acid or other compounds of the formula (I) with the taxane anticancer drugs paclitaxel and docetaxel is therefore expected to have clinical utility in cancer treatment.

The therapeutic methods of the present invention therefore comprise the step of administering to a patient, simultaneously or sequentially, either paclitaxel or docetaxel, and a compound of the formula (I) as defined above or a pharmaceutically acceptable salt or ester thereof.

The compounds of the formula a) are known and can be prepared using methods known to those persons skilled in the art. For example, compounds of the formula (I) and their preparation are described in the following references:

*Journal of Medicinal Chemistry* 34(1): 217–22, January 1991;

*Journal of Medicinal Chemistry* 34(2): 491–6, February 1991;

*Journal of Medicinal Chemistry* 33(5): 1375–9, May 1990;

*Journal of Medicinal Chemistry* 34(9): 2864–70, September 1991; and

*Journal of Medicinal Chemistry* 32(4): 793–9, April 1989, the contents of which are incorporated herein by reference.

The taxanes paclitaxel (taxol) and docetaxel (taxotere) are also well known compounds and can likewise be prepared by methods known to those skilled in the art.

Of the compounds of formula (I) defined above, compounds of the formula (Ia) (in which the substituents $R_1$ and $R_2$ are at the 5- and 6-positions), are generally preferred for use in the methods of the invention. A particularly preferred compound is 5,6-dimethyLxanthenone-4-acetic acid. The preparation of this compound is described in *Journal of Medicinal Chemistry* 34(1): 217–22, January 1991.

The compound of formula (I) and the paclitaxel or docetaxel can be administered to a patient in any suitable form. For example, the compounds may conveniently be administered intravenously, using formulations for each compound already known in the art.

The compounds of formula (I) and the paclitaxel and docetaxel can be administered either simultaneously or sequentially, ie. the taxane can be administered either at the same time, before or after the compound of formula (I) is administered.

It is however generally preferred that the paclitaxel or docetaxel is administered first, followed by administration of the compound of formula (1) as soon as practicable, preferably within about 2–4 hours.

The invention will now be described in more detail with reference to the following non-limiting examples.

EXAMPLES

Example 1

Murine mammary carcinoma MDAH—MCa-4 tumours were grown in female $C_3H$/HeN mice from stocks stored in liquid nitrogen at the sixth transplant generation, and were passaged and used for experiments at the eighth transplant generation. Tumours for experiments were grown by inoculating 20 μl of cell suspension (5 mg packed cells) intramuscularly in the right gastrocenmius muscle. Animals were randomised to treatment groups, and treated with drugs when the dliameter of the tumour-bearing leg reached 10–11 mm (ca 0.6 g tumour), approximately 18 days after inoculation. Drugs were administered once only, by intraperitoneal injection in phosphate buffered saline DMXAA) or chremphor (pacitaxel) using volumes of 0.01 ml/g body weight for each compound. Both compounds were administered essentially at the same time (within 1 min). Host toxicity was assessed by determination of lethality, and by measurement of body weight 4–5 days after drug treatment. The diameter of the tumour-bearing leg was measured three times weekly until values exceeded 13 mm (ca 1.4 g tumour) at which time the animals were terminated. The growth curve for each individual tumour was plotted as in FIG. 1, and the time-to-endpoint (TTE, time from treatment to endpoint) was determined for each mouse. The median and mean TTE was determined for each treatment group. The mean tumour growth delay for each group was calculated as the difference between mean TTE for treated and control groups. The statistical significance of the antitumour effects was tested using ANOVA followed by Dunnett's test to determine p values for the significance of differences between individual groups.

The data in FIG. 1 and Table 1 show that a clear increase in toxicity was seen in the combination, requiring lowering of dose from 42 μmol/kg (not demonstrably toxic for paclitaxel alone) to 31.6 μmol/kg when combined with DMXAA. All mice survived in good health when the latter dose was combined with DMXAA (80 μmol/kg), with no greater weight loss than DMXAA alone. Paclitaxel alone provided little antitumour activity in this model (growth delay of 4 days at 42 μmol/kg), but activity was dramatically enhanced in the combination. Combining taxol at 31.6 μmol/kg with DMXAA provided ⅗ cures, with a mean growth delay of 50 days (42 days longer than DMXAA alone) for the 4 tumours that recurred. Large growth delays were also seen in combination with DMXAA at the two lower taxol dose levels investigated, with one cure at 17.8 μmol/kg Table 1).

TABLE 1

Activity of Paclitaxel and DMXAA, alone and in combination, against the MDAH-MCa-4 tumour. Experimental conditions were as specified above.

| Paclitaxel dose (μmol/kg) | DMXAA dose (μmol/kg) | Expt/ Group Code | Number of mice Treated | Deaths | Cures | % Body Weight change (d4–5) Mean | SEM | Growth delay (days)[a] Mean | SEM | P (rel. To Control) | Growth delay additional to DMXAA only (days)[a] Mean | SEM | p (rel. to DMXAA alone) |
|---|---|---|---|---|---|---|---|---|---|---|---|---|---|
| 0 | 0 | 113/A | 7 | 0 | 0 | 2.1 | 1.3 | 0 | 0.9 | | | | |
| 23.7 | 0 | 113/C | 7 | 0 | 0 | 0.4 | 1.3 | 0 | 1.1 | 1 | | | |
| 31.6 | 0 | 113/D | 7 | 0 | 0 | 1.9 | 0.8 | 0.1 | 1.7 | 1 | | | |
| 42.1 | 0 | 113/E | 7 | 0 | 0 | 0.3 | 1.1 | 4.3 | 1.5 | 0.12 | | | |
| 0 | 80 | 113/B | 7 | 0 | 0 | −4.1 | 1.3 | 8.3 | 2.3 | 0.0002 | | | |
| 17.8 | 80 | 113/Z | 7 | 0 | 1 | −3.8 | 1.3 | 41.7 | 10.0 | | 33.4 | 10.3 | 0.046 |
| 23.7 | 80 | 113/F | 7 | 1 | 0 | −6.7 | 0.7 | 37.6 | 12.7 | | 29.3 | 12.9 | 0.11 |
| 31.6 | 80 | 113/G | 7 | 0 | 3 | −3.9 | 1.2 | 50.5 | 12.8 | | 42.2 | 13.0 | 0.0001 |
| 42.1 | 80 | 113/H | 3 | 3 | 0 | | | | | | | | |

[a]Cured mice are excluded from this analysis

EXAMPLE 2

The effect of varying the time of administration of DMXAA relative to paclitaxel was investigated using the same experimental approach as in Example 1. This experiment is currently in progress, and only an interim analysis is available (based on the median time for tumours to reach the endpoint size). This interim analysis Table 2) confirms the large interaction demonstrated in Example 1. At this time it is not possible to discriminate the magnitude of the response for the groups treated with DMXAA 1 hr before paclitaxel or 1 hr after paclitaxel or 4 hr after paclitaxel or co-administration. The response is not as large with DMXAA administered 4 hr before paclitaxel. This result demonstrates a reasonably broad time window for the interaction.

TABLE 2

Activity of Paclitaxel and DMXAA, alone and in combination, against the MDAH-MCa-4 tumour, with different timing of administration of the two drugs. Experimental conditions were as specified above. This is an interim analysis (animals stilt under observation). For groups with large responses more than half the animals have tumours smaller than the endpoint size and the median is not yet determined.

| Paclitaxel dose (μmol/kg) | DMXAA dose (μmol/kg) | Timing | Expt/ Group Code | Number of mice Treated | Deaths | % Body weight change (d4–5) Mean | SEM | Growth delay (days) Median |
|---|---|---|---|---|---|---|---|---|
| 0 | 0 | | 120/A | 6 | 1 | −1.2 | 1.6 | 0 |
| 0 | 80 | | 120/B | 7 | 2 | −6.0 | 2.7 | 17.9 |
| 23.7 | 0 | | 120/C | 7 | 1 | −0.1 | 4.2 | 3.5 |
| 23.7 | 80 | DMXAA 4 hr after paclitaxel | 120/D | 12 | 4 | −7.4 | 2.4 | >31 |
| 23.7 | 80 | DMXAA 1 hr after paclitaxel | 120/E | 12 | 2 | −5.8 | 3.6 | >41 |
| 23.7 | 80 | Together | 120/F | 12 | 2 | −8.6 | 2.2 | >31 |
| 23.7 | 80 | DMXAA 1 hr before paclitaxel | 120/G | 12 | 0 | −10.1 | 1.1 | >32 |
| 23.7 | 80 | DMXAA 4 hr before paclitaxel | 120/H | 12 | 2 | −9.0 | 1.6 | 31 |

EXAMPLE 3

The interaction of docetaxel with DMXAA was investigated using the same experimental approach as in Example 1, with co-inistration of both compounds in the combination. This experiment is currently in progress, and only an interim analysis is available (based on the median time for tumours to reach the endpoint size). This interim analysis (Table 3) indicates that docetaxel alone is essentially devoid of activity against the MDAH—MCa—4 tumour, but that the combination of docetaxel and DMXAA is much more active than DMXAA alone. Thus, as for paclitaxel, the activity of the combination is much greater than would be expected on the basis of the activities of the single agents.

TABLE 3

Activity of Docetaxel DMXAA, alone and in combination (co-administered), against the MDAH-MCa-4 tumour. Experimental conditions were as specified above. This is an interim analysis (animals still under observation). For groups with large responses more than half the animals have tumours smaller than the endpoint size and the median is not yet determined.

| Docetaxel dose ($\mu$mol/kg) | DMXAA dose ($\mu$mol/kg) | Expt/ Group Code | Number of Mice | | % Body weight change (d4–5) | | Growth delay (days) |
|---|---|---|---|---|---|---|---|
| | | | Treated | Deaths | Mean | SEM | Median |
| 0 | 0 | 120/J | 7 | 1 | 0.58 | 0.74 | 0 |
| 0 | 80 | 120/K | 7 | 0 | −4.8 | 1.3 | 10.5 |
| 17.8 | 0 | 120/L | 2 | 0 | −1.8 | 1.2 | −1.7 |
| 23.7 | 0 | 120/M | 5 | 0 | −4.1 | 1.3 | 0.8 |
| 13.3 | 80 | 120/N | 8 | 0 | −6.8 | 1.5 | 18 |
| 17.8 | 80 | 120/P | 8 | 0 | −7.2 | 1.2 | >21 |
| 23.7 | 80 | 120/Q | 8 | 0 | −7.4 | 1.2 | 26 |

INDUSTRIAL APPLICATION

As will be apparent from the above description and examples, the present invention provides an improved method of cancer therapy which is expected to find widespread clinical utility.

Those persons skilled in the art will understand that the specific description provided thereof is exemplary only and that the present invention is not limited thereto.

What is claimed is:

1. A method of treating cancer, the method comprising the step of administering to a mammal in need of such treatment, either simultaneously or sequentially, an effective amount of (i) a compound which is paclitaxel or docetaxel, and (ii) a compound of the formula

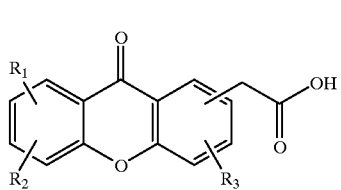

(I)

or a pharmaceutically acceptable salt or ester thereof;
wherein $R_1$, $R_2$ and $R_3$ are each independently selected from the group consisting of H, $C_1$–$C_6$ alkyl, halogen, $CF_3$, CN, $NO_2$, $NH_2$, OH, OR, NHCOR, $NHSO_2R$, SR, $SO_2R$ and NHR wherein each R is independently $C_1$–$C_6$ alkyl optionally substituted with one or more substituents selected from hydroxy, amino and methoxy, and wherein each of $R_1$, $R_2$ and $R_3$ may be present at any of the available positions 1 to 8;
and wherein in each of the carbolyxic aromatic rings in formula (I), up to two of the methine (—CH=) groups may be replaced by an aza (—N=) group;
and wherein any two of $R_1$, $R_2$ and $R_3$ may additionally together represent the group —CH=CH—CH=CH—, such that this group, together with the carbon or nitrogen atoms to which it is attached, forms a fused 6 membered aromatic ring, wherein said cancer is sensitive to the combination of (i) and (ii), and
wherein an anticancer effect is achieved with a combination of a compound of formula (I) and paclitaxel which is larger than the anticancer effect achieved with either said compound of formula (I) or paclitaxel alone and exceeds the sum of the effects of said compound of formula (I) and paclitaxel, and
wherein an anticancer effect is achieved with a combination of a compound of formula (I) and docetaxel which is larger than the anticancer effect achieve with either said compound of formula (I) or docetaxel alone and exceeds the sum of the effects of said compound of formula (I) and docetaxel.

2. A method as claimed in claim 1, wherein the mammal is a human.

3. A method as darned in claim 1, wherein the compound of formula (1) is of the formula

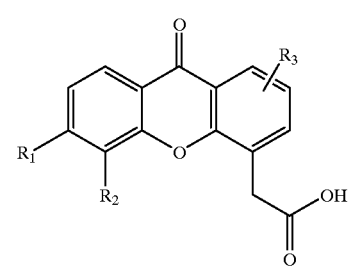

(Ia)

or a pharmaceutically acceptable salt or ester thereof.

4. A method as claimed in claim 3, wherein the compound of formula (Ia) is 5,6-dimethylxanthenone-4-acetic acid or a pharmaceutically acceptable salt or ester thereof.

5. A pharmaceutical composition suitable for treating cancer, comprising a compound of the formula (I) as defined in claim 1 or a pharmaceutically acceptable salt or ester thereof, and a compound which is paclitaxel or docetaxel, in combination with one or more pharmaceutically acceptable carriers or vehicles, wherein the cancer is sensitive to the combination of the compound of formula (I) and paclitaxel or the compound of formula (I) and docetaxel, and
wherein an anticancer effect is achieved with a combination of a compound of formula (I) and paclitaxel which is larger than the anticancer effect achieved with either said compound of formula (I) or paclitaxel alone and exceeds the sum of the effects of said compound of formula (I) and paclitaxel, and wherein an anticancer effect is achieved with a combination of a compound of formula (I) and docetaxel which is larger than the anticancer effect achieved with either said compound of formula (I) or docetaxel alone and exceeds the sum of the effects of said compound of formula (I) and docetaxel.

* * * * *

UNITED STATES PATENT AND TRADEMARK OFFICE
CERTIFICATE OF CORRECTION

PATENT NO. : 6,667,337 B2
DATED : December 23, 2003
INVENTOR(S) : Wilson

It is certified that error appears in the above-identified patent and that said Letters Patent is hereby corrected as shown below:

Column 1,
Line 10, please delete "5,6-dimethylanthenone-4-acetic acid" and insert -- 5,6-dimethylxanthenone-4-acetic acid --;
Line 11, please delete "PMAA" and insert -- DMXAA --;
Line 51, please delete "R3" and insert -- $R_3$ --;
Line 53, please delete "CF3, CN, NO2, NH2" and insert -- $CF_3$, CN, $NO_2$, $NH_2$ --;
Line 54, please delete "SO2R" and insert -- $SO_2R$ --;
Line 55, please delete "C1-C6 alkyl" and insert -- $C_1$-$C_6$ alkyl --;
Line 57, please delete "R1, R2 and R3" and insert -- $R_1$, $R_2$ and $R_3$ --;

Column 2,
Line 66, please delete "80 $\mu$mol/lcg" and insert -- 80 $\mu$mol/kg --;
Line 66, please delete "pachitaxel" and insert -- paclitaxel --;

Column 3,
Line 30, please delete "formula a )" and insert -- formula (l) --;
Line 53, please delete "5,6-dimethyLxanthenone-4-acetic acid" and insert -- 5,6-dimethylxanthenone-4-aceitc acid --;

Column 4,
Line 30, please delete "DMXAA)" and insert -- (DMXAA) --;
Line 31, please delete "(pacitaxel)" and insert -- (paclitaxel) --;
Line 39, please delete "FIG 1" and insert -- Figure 1 --;

UNITED STATES PATENT AND TRADEMARK OFFICE
CERTIFICATE OF CORRECTION

PATENT NO. : 6,667,337 B2
DATED : December 23, 2003
INVENTOR(S) : Wilson

It is certified that error appears in the above-identified patent and that said Letters Patent is hereby corrected as shown below:

<u>Columns 5 and 6,</u>
Table 2, line 3, please delete "(animals stilt under observation)" and insert
-- (animals still under observation) --;

<u>Column 6,</u>
Example 3, line 3, please delete "with co-inistration" and insert -- with co-administration --.

Signed and Sealed this

Sixth Day of July, 2004

JON W. DUDAS
*Acting Director of the United States Patent and Trademark Office*